United States Patent [19]

Kim

[11] Patent Number: 4,625,026

[45] Date of Patent: Nov. 25, 1986

[54] 2-AMINO-4-OXO-TRICYCLICPYRIMIDINES HAVING ANTIVIRAL ACTIVITIES AGAINST HERPES SIMPLEX VIRUS TYPE II INFECTIONS

[75] Inventor: Sun H. Kim, Chestnut Hill, Mass.

[73] Assignee: Biomeasure, Inc., Hopkinton, Mass.

[21] Appl. No.: 541,777

[22] Filed: Oct. 13, 1983

Related U.S. Application Data

[63] Continuation-in-part of Ser. No. 454,732, Dec. 30, 1982, abandoned.

[51] Int. Cl.$^4$ .................. C07D 487/00; A61K 31/505
[52] U.S. Cl. .................................... 544/249; 514/268; 544/287; 544/253; 424/28
[58] Field of Search ............... 544/249, 250, 253, 287; 424/251; 514/268

[56]         References Cited
     U.S. PATENT DOCUMENTS

| | | | |
|---|---|---|---|
| 3,057,467 | 10/1962 | Williams | 206/46 |
| 3,185,691 | 5/1965 | Pribyl | 260/256.4 |
| 3,257,400 | 6/1966 | Wagner | 260/256.4 |
| 3,398,826 | 8/1968 | Clancy | 206/46 |
| 3,609,152 | 10/1971 | Hess et al. | 260/256 |
| 3,786,615 | 1/1974 | Bauer | 53/21 |
| 3,941,787 | 3/1976 | Salmond | 544/249 |

FOREIGN PATENT DOCUMENTS 47-42271 10/1972 Japan .

*Primary Examiner*—Donald G. Daus
*Assistant Examiner*—Cecilia Shen

[57]           ABSTRACT

In one aspect, compounds having antiviral activity and having the general formula:

wherein each $R^2$, independently, is H or lower (fewer than 6 carbon atoms) alkyl; each $R^3$, independently, is H or lower alkyl $R^0$ is H or lower alkyl, $R^1$ is H or lower alkyl; $1 \leq n \leq 11$; $n-2 \leq m \leq 2n$; $0 \leq p \leq 3$; z is 0 or 1; and $p \leq q \leq 2p$; each n, m, p and q being selected so that the sp$^3$ valence shell of each carbon atom in each ring is filled; or a pharmaceutically acceptable salt thereof.

9 Claims, 1 Drawing Figure

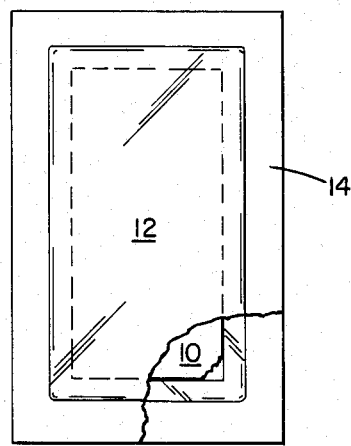

2-AMINO-4-OXO-TRICYCLICPYRIMIDINES HAVING ANTIVIRAL ACTIVITIES AGAINST HERPES SIMPLEX VIRUS TYPE II INFECTIONS

BACKGROUND OF THE INVENTION

This application is a continuation-in-part of Kim U.S. patent application Ser. No. 454,732, filed Dec. 30, 1982, now abandoned.

This invention relates to antiviral compounds.

SUMMARY OF THE INVENTION

In general, the invention features, in one aspect, compounds having in vivo antiviral activity and having the general formula:

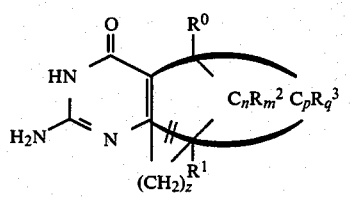

wherein each $R^2$, independently, is H or lower (fewer than 6 carbon atoms) alkyl; each $R^3$, independently, is H or lower alkyl; $R^0$ is H or lower alkyl, $R^1$ is H or lower alkyl; $1 \leq n \leq 11$; $n-2 \leq m \leq 2n$; $0 \leq p \leq 3$; z is 0 or 1; and $p \leq q \leq 2p$; each n, m, p and q being selected so that the $sp^3$ valence shell of each carbon atom in each ring is filled; or a pharmaceutically acceptable salt thereof.

In preferred embodiments, the antiviral compound is 2-amino-4-oxo-5, 6, 7, 8-tetrahydroquinazoline; 2-amino-5, 6, 7, 8, 9-pentahydrocyclohepta (d) pyrimidin-4-ol; or 2-amino-5, 6, 7, 8, 9, 10, 11, 12, 13, 14-decahydro-cyclododeca (d) pyrimidin-4-ol.

In another aspect, the invention features antiviral compounds having antiviral activity and having the general formula

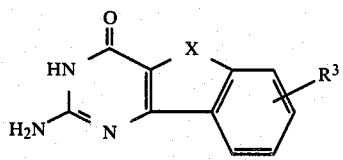

wherein X is $(CH_2)_n$ where 1 n 3,

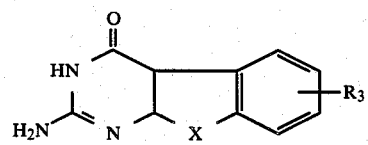

where $R^4$ is lower alkyl; $CH_2S$; or $CH_2O$; $R^3$ is H, lower alkyl, lower alkoxy (lower alkyl also containing oxygen), a halogen, C=N, nitro, amino, lower alkylamino, lower dialkylamino, lower arylamino, carboxy, lower alkoxycarbonyl (containing an ester linkage); provided that, when X is $(CH_2)_2$, $R_3$ cannot be H; or a pharmaceutically acceptable salt thereof.

In a preferred embodiment the antiviral compound is 2-amino-4-oxo-5, 6, 7-trihydrobenzocyclohepta (5, 6-d)-pyrimidine.

In another aspect the invention features compounds having antiviral activity and having the general formula:

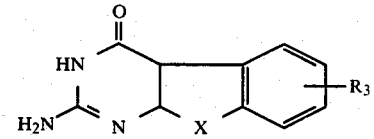

wherein X and $R_3$ are as defined above for Formula (2) except $R_3$ can be H when X is $(CH_2)_2$, or a pharmaceutically acceptable salt thereof.

In another aspect, the invention features treating a mammal suffering from a viral infection, preferably a herpes infection, most preferably a herpes simplex type II viral infection, by administering to the mammal an antivirally effective amount of 2-amino-4-oxo-3, 4, 5, 6-tetrahydrobenzo (h) quinazoline, or a pharmaceutically acceptable salt thereof.

The compounds exhibit potent antiviral activity, are chemically stable, are not toxic to mammals, and do not decompose in the stomach. The compounds can be particularly valuable in the treatment of immunocompromised patients, e.g. cancer patients, who are at risk of contracting viral infections, particularly herpes simplex virus type II infections.

Other features and advantages of the invention will be apparent from the following description of the preferred embodiments, and from the claims.

DESCRIPTION OF THE PREFERRED EMBODIMENTS

We turn now to a description of preferred embodiments of the invention.

DRAWING

The FIGURE is a plan view, partially broken away, of a packet containing a towlette impregnated with an antiviral compound of the invention.

STRUCTURE

The compounds have the general formulae recited in the Summary of the Invention above. Examples of preferred compounds within those formulae are those referred to as preferred embodiments above.

The compounds all have an aminopyrimidone ring fused to a non-aroma ring. A third ring can also be present.

For Formula (1) compounds, where there is no third ring present, the non-aromatic ring can have up to 15 carbon atoms. When there is a third ring present, the second ring will generally have fewer carbon atoms, i.e. 6 or less; i.e. n will be 1 or 2 when p is greater than 0.

The compounds, or pharmaceutically acceptable salts thereof, can be administered alone or in combination with a pharmaceutically acceptable carrier.

Acceptable salts include those made with, e.g., hydrochloric, hydrobromic, hydroiodic, sulfuric, maleic, or fumaric acid; or with potassium, sodium hydroxide, or dicyclohexylamine.

For oral administration the pharmaceutical composition can most conveniently be in the form of capsules or tablets. The composition can also take the form of an ingestible liquid, e.g., syrup. The compounds can also be provided in the form of topical preparations, e.g., ointments, lotions, creams, powders, and sprays.

Referring now to the FIGURE, flexible sheet 10 of fibrous, absorbant paper can be impregnated with an antiviral compound of the invention, diluted, if desired, with a carrier, e.g. distilled water. The impregnated towelette 10 is folded and enclosed in rectangular, sealed, gas tight envelope 12, having fused periphery 14, in a manner such as is described in Clancy U.S. Pat. No. 3,398,826 or Williams U.S. Pat. No. 3,057,467, hereby incorporated by reference. The towlette is impregnated using conventional techniques, e.g. that disclosed in Bauer U.S. Pat. No. 3,786,615, hereby incorporated by reference.

SYNTHESIS

To synthesize a compound of Formula 1, 2, or 3, a mixture of the appropriate alpha-ketoester and guanidine carbonate in xylene is refluxed overnight, and the final product is then collected by filtration and purified.

The alpha-ketoester, if not commercially available, can be prepared by any of several methods, e.g., the reaction of a cyclic ketone with diethyloxalate followed by pyrolysis; or esterification of the commercially available alpha-keto acid, e.g. camphor carboxylic acid; or the reaction of a cyclic ketone with diethylcarbonate at elevated temperature in the presence of guanidine salts in an appropriate solvent, e.g., alcohols, xylene, toluene.

General references describing the synthesis of alpha-ketoesters can be found in *The Pyrimidines*, A. Weissberger, Ed., Interscience, New York, 1962; J. Org. Chem., 30, 1837 (1965); J. Org. Chem. 33, 4288 (1968); J. Het. Chem. 7, 197 (1970); J. Het Chem., 13, 675 (1976); Org. Syn. 47, 20 (1967).

Another method of synthesizing a compound of Formula 1, 2, or 3 involves the formation of a 2, 4-diaminopyrimidine derivative by the reaction of a cyclic ketone with dicyandiamide, either in the absence of or in an appropriate solvent, e.g., dimethylformamide, ethoxyethoxyethanol, followed by selective hydrolysis of one amino group.

Specific compounds of Formula (1) were made as follows.

2-amino-4-oxo-5, 6, 7, 8-tetra-hydroquinazoline

A mixture of ethyl-2-cyclohexanone carboxylate (2.0 g) and guanidine carbonate (2.66 g) in xylene (40 ml) was refluxed overnight; after cooling the solid was collected by filtration, washed with water, methanol, and dried over $MgSO_4$. 0.6 g of a white solid having a m.p. >300° C. was recovered. The solid was dissolved in Con. HCl, and excess HCl was removed in vacuo to dryness. The gummy residue was treated with methanol-ether to afford a colorless plate (0.6 g).

2-amino-5, 6, 7, 8, 9 pentahydro cyclohepta (d) pyrimidin-4-ol

A mixture of ethyl-2-cycloheptanone carboxylate (880 mg) and guanidine carbonate (950 mg) in xylene (20 ml) was refluxed overnight; after cooling, the white solid was collected by filtration, washed with water, and dried. The crude product was recrystallized from methanol. Mass: 179 (mol. ion).

2-Amino-5, 6, 7, 8, 9, 10, 11, 12, 13,14-decahydrocyclododeca (d) pyrimidin-4-ol A mixture of ethyl-2-cyclododecanone carboxylate (4.0 g) and guanidine carbonate (3.12 g) in xylene (50 ml) was refluxed overnight; after cooling the white solid was collected by filtration, washed with water, and recrystallized from ethanol. 2.15 g of a white powder were recovered.

2-amino-5, 6, 7, 8, 9, 10-hexahydrocycloocta (d) pyrimidin-4-ol

A mixture of ethyl-2-cyclooctanone carboxylate (3.5 g) and guanidine carbonate (3.82 g) in xylene (50 ml) was refluxed overnight; after cooling the white solid was collected by filtration, washed with water, and dried to yield 2.0 g of product.

A specific compound of Formula (2) was made as follows.

2-amino-4-oxo-5, 6, 7-trihydrobenzocycohepta (5, 6-d)-pyrimidine

First 2-ethoxycarbonyl-1-benzosuberone was prepared by placing 3.4 g of 50% NaH mineral oil dispersion in a 250 ml three-necked flask, fitted with an additional funnel and a water condenser, under a nitrogen atmosphere. The mineral oil was removed by washing with dry benzene several times, and the residue was then resuspended in dry benzene (34 ml). Diethylcarbonate (5.9 g) was then added all at once. After reflux the mixture was treated with dropwise addition of a solution of 1-benzosuberone (4.0 g) in dry benzene (10 ml) over a 3 hour period, and refluxing was continued for another ½ hour. The mixture was cooled to room temperature, treated with acetic acid (5 ml) and ice-water (17 ml) to dissolve the solid, and the organic layer was then washed with water several times and then dried ($MgSO_4$). After evaporation of solvent the residue was subjected to fractional distillation to give a colorless oil product (3.12 g) at 135–140/0.3 mm Hg.

A mixture of 2-ethoxycarbonyl-1-benzosuberone (2.82 g), guanidine carbonate (2.62 g) in xylene (50 ml) was refluxed overnight. After cooling to room temperature, the resulting solid was collected by filtration, washed with water and then ether and then dried. The solid was redissolved in 2N-HCl with heating, then cooled in an ice bath. The white precipitate was collected by filtration, washed with ether, then dried to yield a white powder (900 mg).

2-amino-4-oxo-3, 4, 5, 6-tetrahydrobenzo (h) quinazoline

First, 2-ethoxycarbonyl-1-tetralone was made by placing 4.65 g of 50% NaH mineral oil dispersion in a 250 ml three-necked flask, fitted with an additional funnel and a water condenser, under a nitrogen atmosphere. The mineral oil was removed by washing with dry benzene several times and NaH was then resuspended in dry benzene (48 ml), and diethylcarbonate (8.1 g) was added all at once. After refluxing, the mixture was treated with a dropwise addition of a solution of alpha-tetralone (5 g) in dry benzene (1 ml) over a 3 hour period, and refluxing was continued for another ½ hour. The mixture was cooled to room temperature, treated with acetic acid (7 ml) and ice-water (23 ml) to dissolve solid and organic layers, washed with water several times, dried (using anhydrous $MgSO_4$). After evaporation of solvent, the residue was subjected to fractional distillation to yield product (2.3 g) at 151–157/0.2 mm Hg.

A mixture of 2-ethoxycarbonyl-1-tetralone (0.65 g) and guanidine carbonate (0.65 g) in xylene (15 ml) was refluxed overnight and, after cooling to room temperature, the tan solid was collected by filtration, washed with water and alcohol, and then dried to yield 0.24 g of tan solid, m.p.>300° C. The solid was dissolved in Con.-HCl, concentrated in vacuo to dryness, and recrystallized from ethanol to yield a colorless solid product, (0.28 g).

USE

When administered to mammals (e.g., orally, nasally, topically, parenterally, intravenously, or by suppository), the compounds have an antiviral effect, and are particularly effective against herpes simplex viruses occurring in the eye, cutaneously, orally, genitally, or in upper respiratory areas.

Good in vivo test results, compared to in vitro results, suggest that the compounds, rather than acting directly on the virus, act via some other mechanism, e.g. immunomodulation or inducement of interferon production.

The compounds can be administered to a mammal, e.g. a human, in a dosage of 25 to 300 mg/kg/day, preferably 100 to 200 mg/kg/day.

Referring again to the FIGURE, when it is desired to apply an antiviral compound topically, sealed envelope 12 containing the impregnated towlette 10 is torn open and the towlette is removed and used, and the packet and used towlette are then discarded.

The impregnated towlette can be used in the treatment and or prevention of herpes simplex type II infections. In the case of the treatment of a skin lesion associated with herpes, the impregnated towlette can be used to apply the antiviral compound to the affected area and then discarded. For prevention of herpes infections, the impregnated towlette can be used to apply the antiviral compound to an area which the user suspects has been recently exposed to herpes virus, e.g., to the genitals following sexual relations.

OTHER EMBODIMENTS

Other embodiments are within the following claims. For example, the impregnated sheet can be, in addition to absorbant paper, another suitable material such as unwoven fabric. Instead of sealing wet towlettes in individual packets, multiple impregnated sheets can be provided in one container, e.g. a jar or a metal or plastic can. Impregnated towlettes can be used to treat or prevent other viral infections, e.g. the common cold; for treatment of colds, for example, facial tissues could be impregnated with an antiviral compound, application of the tissue to the nose providing the antiviral compound to that area.

I claim:

1. A compound having in vivo antiviral activity and having the formula:

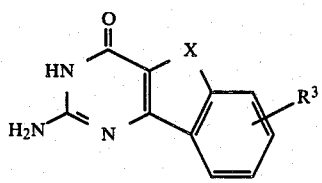

wherein
X is $(CH_2)_3$; or

where $R^4$ is lower alkyl having between 1 and 6 carbon atoms, inclusive; and
$R^3$ is H, lower alkyl having between 1 and 6 carbon atoms, inclusive, lower alkoxy having between 1 and 6 carbon atoms, inclusive, a halogen, or $C\equiv N$;
or a pharmaceutically acceptable salt thereof.

2. A compound having in vivo antiviral activity and having the formula:

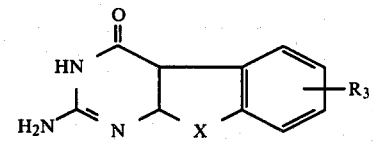

wherein
X is $(CH_2)_3$; or

where $R_4$ is lower alkyl having between 1 and 6 carbon atoms, inclusive; and
$R^3$ is H, lower alkyl having between 1 and 6 carbon atoms, inclusive, lower alkoxy having between 1 and 6 carbon atoms, inclusive, halogen, or $C\equiv N$;
or a pharmaceutically acceptable salt thereof.

3. The compound of claim 1, wherein X is $(CH_2)_3$ and $R_3$ is H;
said compound having the formula 2-amino-4-oxo-5, 6, 7-trihydrobenzocyclohepta (5, 6-d)-pyrimidine.

4. An antiviral compound having the formula 2-amino-5,6,7,8,9 pentahydrocyclohepta (d) pyrimidin-4-ol, or a phamaceutically acceptable salt thereof.

5. An antiviral composition comprising an antivirally effective amount of the compound of claims 1 or 2, together with a pharmaceutically acceptable carrier substance.

6. The composition of claim 5 wherein said composition is in the form of a pill, capsule, or tablet for oral administration to a human patient in need of said compound for treatment of a herpes simplex type II infection.

7. The composition of claim 5 wherein said composition is in the form of an ointment, lotion, cream, powder, gel, or spray for application to the skin of a human patient in need of said compound for treatment of a viral infection.

8. A method of treating a mammal suffering from a herpes simplex type II infection comprising administering to said mammal a therapeutically effective amount of the compound of any one of claims 1 or 2.

9. A method of treating a mammal suffering from a herpes simplex type II infection comprising administering to said mammal an antivirally effective amount of
2-amino-4-oxo-3,4,5,6-tetrahydrobenzo (h) quinazoline;
or a pharmaceutically acceptable salt thereof.

* * * * *